US010111441B1

(12) United States Patent
Awad et al.

(10) Patent No.: US 10,111,441 B1
(45) Date of Patent: Oct. 30, 2018

(54) SYNTHESIS OF SILVER-PMMA NANOCOMPOSITE FILM USING HERBAL EXTRACT

(71) Applicant: KING SAUD UNIVERSITY, Riyadh (SA)

(72) Inventors: Manal Ahmed Gasmelseed Awad, Riyadh (SA); Awatif Ahmed Hendi, Riyadh (SA); Khalid Mustafa Osman Ortashi, Riyadh (SA); Dina Wafiq Awad Soliman, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 15/956,675

(22) Filed: Apr. 18, 2018

(51) Int. Cl.

| | |
|---|---|
| ***A01N 65/08*** | (2009.01) |
| ***C08J 5/18*** | (2006.01) |
| ***A01N 25/10*** | (2006.01) |
| ***C02F 1/50*** | (2006.01) |
| ***A01N 59/16*** | (2006.01) |
| ***A61K 9/16*** | (2006.01) |

(52) U.S. Cl.
CPC ............ *A01N 65/08* (2013.01); *A01N 25/10* (2013.01); *A01N 59/16* (2013.01); *A61K 9/1652* (2013.01); *C02F 1/50* (2013.01); *C08J 5/18* (2013.01); *C02F 2305/08* (2013.01); *C08J 2333/12* (2013.01)

(58) Field of Classification Search
None
See application file for complete search history.

(56) References Cited

U.S. PATENT DOCUMENTS

2015/0024204 A1* 1/2015 Amanchi Bala ...... B22F 1/0018 428/402

FOREIGN PATENT DOCUMENTS

| | | | |
|---|---|---|---|
| CN | 105248473 | A | 1/2016 |
| CN | 106266133 | A | 1/2017 |
| JP | 57-56415 | A | 4/1982 |

OTHER PUBLICATIONS

Kong et al., "Antibacterial properties of novel poly(methyl methacrylate) nanofiber containing silver nanoparticles," Langmuir, Mar. 4, 2008;24(5): 2051-6, Epub Jan. 29, 2008.

Angalaparameswari et al., "Anti-microbial Activity of Aristolochic Acid from Root of Aristolochia bracteata Retz," World Academy of Science, Engineering and Technology, 57, 2011.

Singho, N.D. et al., "Enhancement of the Refractive Index of Silver Nanoparticles in Poly (Methyl Methacrylate)", Int. J. of Res. in Engineering and Technology (IJRET), vol. 1, No. 4, pp. 231-234, 2012.

* cited by examiner

*Primary Examiner* — Susan T Tran
(74) *Attorney, Agent, or Firm* — Richard C. Litman

(57) ABSTRACT

The synthesis of a silver-PMMA nanocomposite film using herbal extract includes mixing an aqueous extract of *Aristolochia bracteolate* buds with an aqueous solution of silver nitrate, thereby reducing the silver ions to silver metal nanoparticles. A solution of the silver nanoparticles is added to a solution of PMMA [poly (methyl methacrylate)] in N'N-dimethylformamide (DMF) with stirring at 80° C. A brown solution of silver colloids develops, which is cast in a glass plate and the DMF is evaporated at room temperature, leaving a silver-PMMA nanocomposite film. Testing on water shows the silver-PMMA nanocomposite film prevents or inhibits growth of microbes, suggesting use as an antimicrobial or antibacterial agent, e.g., in water purification. In addition, testing by disc diffusion against *E. coli* and *Bacillus cereus* showed zones of inhibition, also suggesting use as an antimicrobial or antibacterial agent.

7 Claims, 6 Drawing Sheets

SYNTHESIS OF SILVER-PMMA NANOCOMPOSITE FILM USING HERBAL EXTRACT

BACKGROUND

1. Field

The disclosure of the present patent application relates to polymer/metal nanoparticle composites, and particularly to the synthesis of a silver-PMMA nanocomposite film using an herbal extract wherein the silver nanoparticles are synthesized using green chemistry, the resulting nanocomposite having antibacterial properties suitable for water purification and other applications.

2. Description of the Related Art

Silver nanoparticles have unique optical, electrical, and thermal properties and are being incorporated into products that range from photovoltaics to biological and chemical sensors. Examples include conductive inks, pastes and fillers which utilize silver nanoparticles for their high electrical conductivity, stability, and low sintering temperatures. Additional applications include molecular diagnostics and photonic devices, which take advantage of the novel optical properties of these nanomaterials. An increasingly common application is the use of silver nanoparticles for antimicrobial coatings, and many textiles, keyboards, wound dressings, and biomedical devices now contain silver nanoparticles that continuously release a low level of silver ions to provide protection against bacteria.

Polymers are thought to be an amazing host material for metallic nanoparticles. The polymer acts as a surface topping specialist when the nanoparticles are implanted into them. The resulting nanocomposites may display improved optical properties.

The properties of such polymer composites depend on the particular type of incorporated nanoparticles, as well as their size and shape, concentration, and interaction with the polymer matrix. Among polymer materials, PMMA is well known for use as a polymeric glass, with a wide range of applications. Use of PMMA typically makes available carboxylate functional groups that may help provide chemical bonding with the metal ions, while the high level of solubility of PMMA in solvents like DMF helps facilitate silver nitrate reduction, if needed.

Silver nanoparticles (AgNPs) have been shown to form composites with polymers, such as polyvinyl alcohol, polypyrrole, polyvinylidene fluoride, chitosan, and cellulose. The formation of polymer-silver nanocomposites requires that the size of the nanoparticles in the polymer matrix be controllable, and that their distribution within the polymer matrix be uniform.

Nanomaterials can be synthesized by different methods, including chemical, physical, and biological methods. Some chemical and physical methods have resulted in or contributed to environmental contamination, since the chemical procedures involved can generate a large amount of hazardous byproducts. Thus, there is a need to continue to develop new "green" synthesis procedures for nanoparticles that are clean, safe, ecofriendly, and nontoxic, without the use of high pressure, energy, temperature, and toxic chemicals. The biological methods include synthesis of nanomaterials from the extracts of plant, bacterial, and fungal species, among other procedures.

The plant *Aristolochia bracteolate*, also known as Um-Jalajel, is an herb found in the sub-Saharan regions of Africa, through the Arabian peninsula to India. In traditional medicine, the extracts of some parts of the plant are believed to exhibit antibacterial properties.

Thus, the synthesis of a silver-PMMA nanocomposite film using herbal extract solving the aforementioned problems is desired.

SUMMARY

The synthesis of a silver-PMMA nanocomposite film using herbal extract includes mixing an aqueous extract of *Aristolochia bracteolate* buds with an aqueous solution of silver nitrate, thereby reducing the silver ions to silver metal nanoparticles. A solution of the silver nanoparticles is added to a solution of PMMA [poly (methyl methacrylate)] in N'N-dimethylformamide (DMF) with stirring at 80° C. A brown solution of silver colloids develops, which is cast in a glass plate and the DMF is evaporated at room temperature, leaving a silver-PMMA nanocomposite film. Testing on water shows the silver-PMMA nanocomposite film prevents or inhibits growth of microbes, suggesting use as an antimicrobial or antibacterial agent, e.g., in water purification. In addition, testing by disc diffusion against *E. coli* and *Bacillus cereus* showed zones of inhibition, also suggesting use as an antimicrobial or antibacterial agent.

These and other features of the present disclosure will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The synthesis of a silver-PMMA nanocomposite film using an herbal extract of *Aristolochia bracteolate* buds to synthesize the silver nanoparticles and subsequent synthesis of the polymer nanocomposite film, and analysis of the antimicrobial activity of the nanocomposite, is set forth below.

Example 1

Preparation of Greener Silver Nanoparticles

We collected *Aristolochia bracteolate* (also known as Um-Jalajel) buds from a rural part of the Kabooshia area in Sudan. We took 5 g of the buds, and cleaned, washed, dried, and ground them. We soaked the ground, dried buds in boiled distilled water overnight. The extract was filtered, and the filtrate was immediately used to prepare silver nanoparticles. The filtrate was treated with an aqueous solution of silver nitrate ($AgNO_3$), which was first prepared as follows.

An aqueous solution of silver nitrate ($AgNO_3$), was prepared by dissolving 1 mmol/ml of silver nitrate in 50 ml of distilled water. The filtrate from above was added to the aqueous silver nitrate solution, with vigorous stirring at 60° C. for 10 minutes. The colloidal solution changed in color from colorless to yellow, as noted by visual observation, confirming reduction of the silver ions and formation of the silver nanoparticles (AgNPs). Then the resulting greener nanoparticle solution was incubated at room temperature until it was used.

Figure 1A:
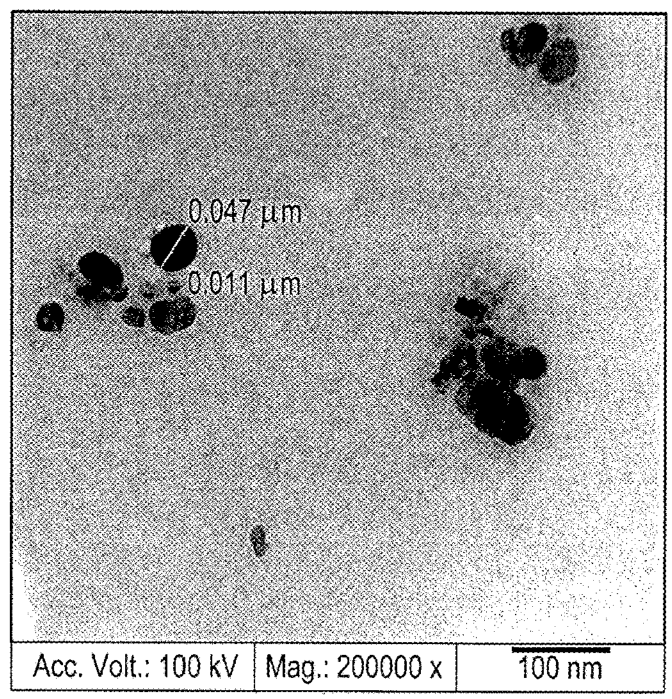
FIG. 1A is a TEM (transmission electron microscopy) micrograph of the silver nanoparticles prepared using *Aristolochia bracteolate* extract, the scale bar corresponding to 100 nm.
Figure 1B:
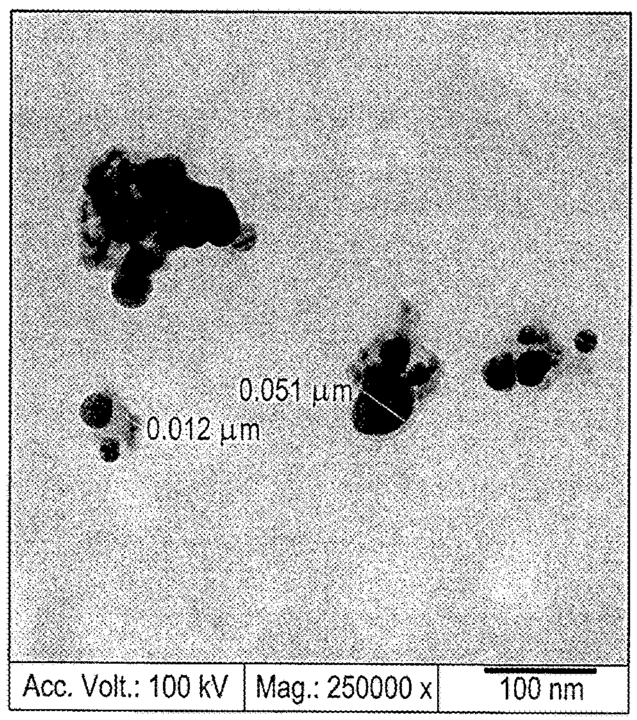
FIG. 1B is another TEM micrograph of the silver nanoparticles prepared using *Aristolochia bracteolate* extract, the scale bar corresponding to 100 nm.

We employed transmission electron microscopy (TEM) using a JEM-1011 transmission electron microscope, obtained from JEOL, in Japan, to characterize the size, shape, and morphology of the synthesized silver nanoparticles, using accelerating voltage of 100 KV. See FIGS. 1A and 1B. The silver nanoparticles had sizes between 12 nm and 50 nm.

Example 2

Synthesis of Silver-PMMA Nanocomposite Film

We obtained PMMA [poly (methyl methacrylate)] from SABIC Company, in Saudi Arabia. We dissolved 6 g of the PMMA in N',N-dimethylformamide (DMF) obtained from R & M Marketing, in Essex, UK. A freshly prepared solution of the silver nanoparticles was added to the PMMA solution. The addition was carried out in a hood under constant stirring at 80° C. The mixture was stirred for 1 hour in order to complete the reaction.

The resulting solution was light brown, due to the formation of silver colloids. The solution was then cast onto glass plate. The DMF was evaporated at room temperature, resulting in the nanocomposite film. Once dry, the film was removed from the glass plate.

Figure 2A:
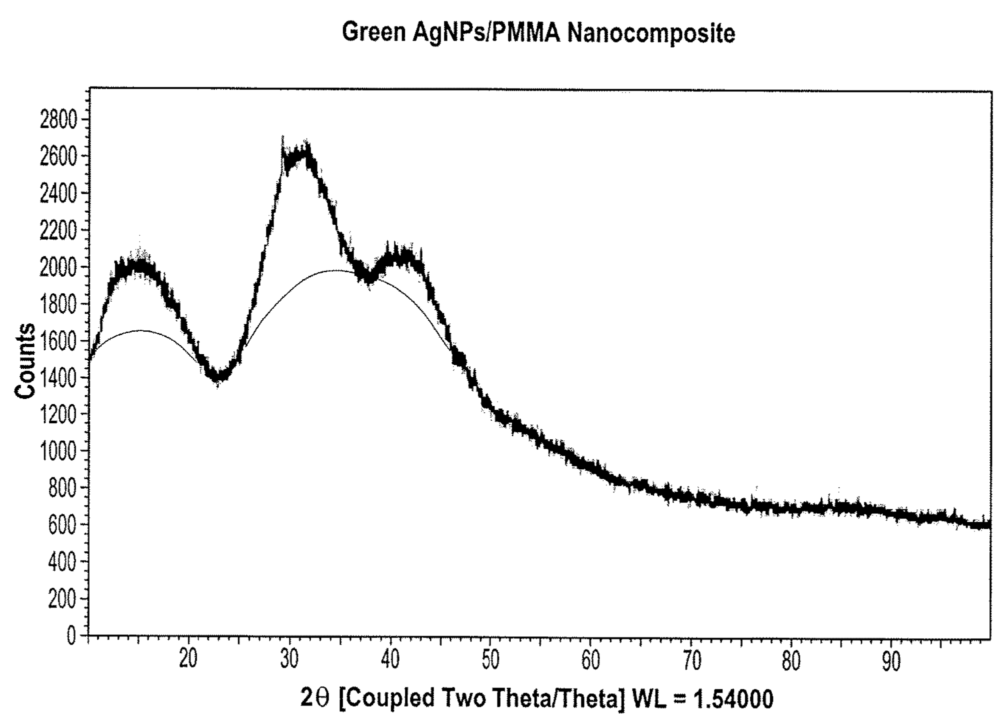
FIG. 2A shows the XRD analysis results of silver-PMMA nanocomposite film, synthesized as described herein.
Figure 2B:
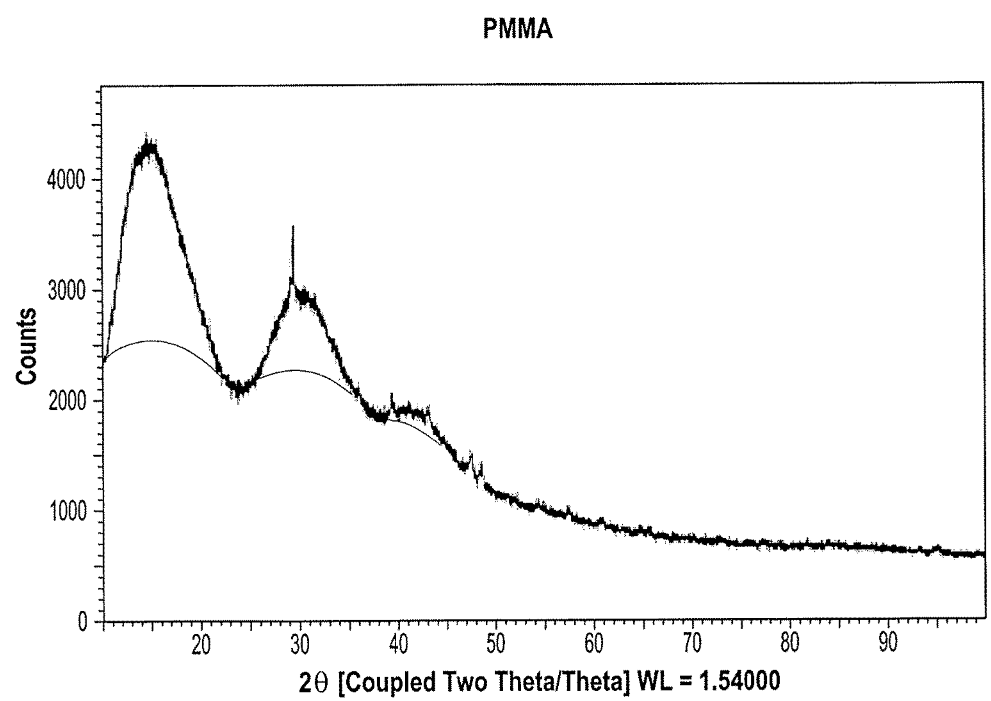
FIG. 2B shows the XRD analysis results of pure PMMA polymer film.

X-ray diffraction (XRD) was performed on a Bruker D8 Discover, to examine and compare the greener AgNPs/PMMA nanocomposite and PMMA films. See FIGS. 2A and 2B.

Figure 3:
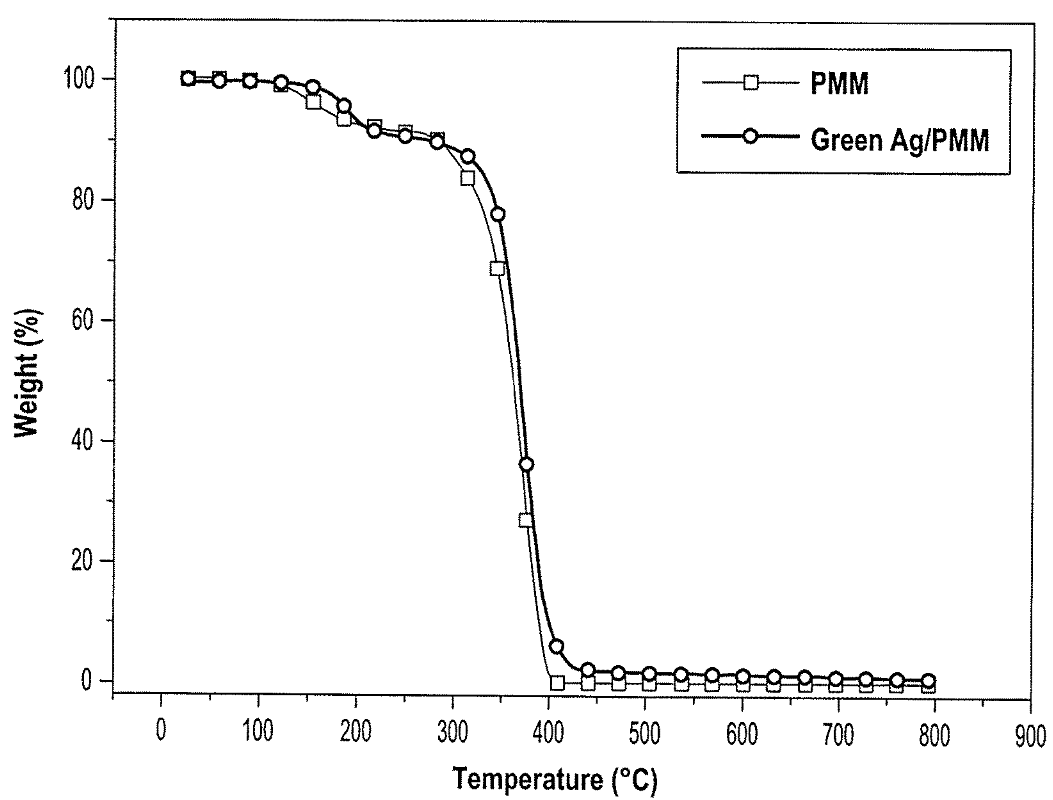
FIG. 3 is a composite plot of TGA (thermogravimetric analysis) thermograms for pure PMMA polymer and the silver-PMMA nanocomposite film, synthesized as described herein.

TGA (thermogravimetric analysis) thermograms were carried out on a Mettler Toledo TGA/DSC 1, providing comparison between the greener AgNPs/PMMA nanocomposite and PMMA films. See FIG. 3. About 4 mg of dried film per sample was used for the TGA comparison. TGA thermograms were obtained through a range of 0-800° C. under nitrogen air flow at a rate of 10° C./min. The distinct graphs were plotted with weight (percentage) loss against temperature.

Example 3

Antimicrobial Study

Figure 4:
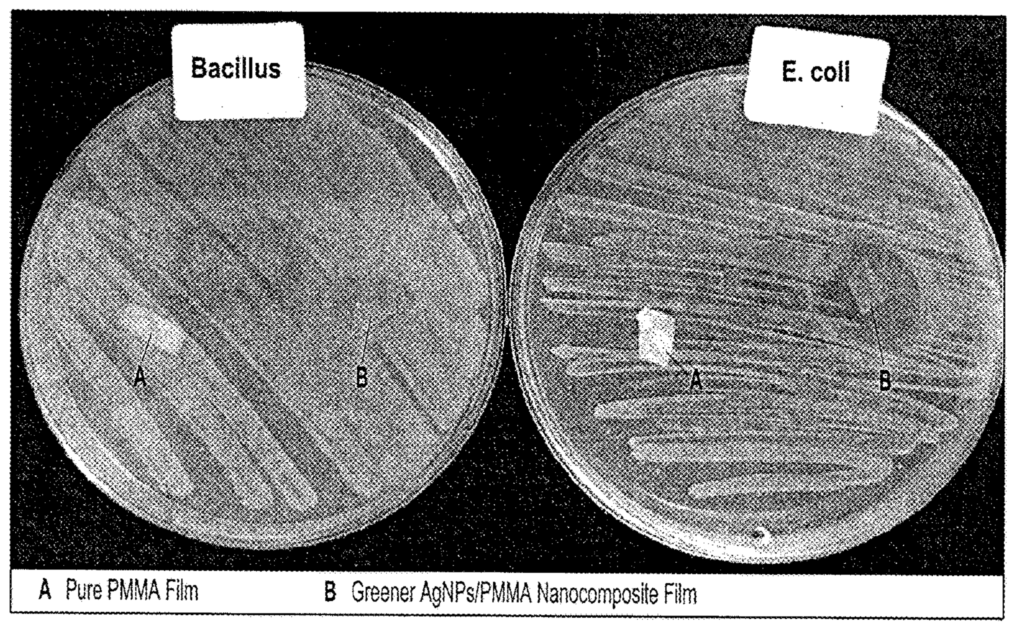
FIG. 4 is a photograph of cultures of *Bacillus cereus* and *E. coli*, comparing the effect of treatment with a pure PMMA film (A) with a silver-PMMA nanocomposite film (B), synthesized as described herein.

The antibacterial activity of the silver-PMMA nanocomposite film was evaluated against both a gram-negative bacteria, *Escherichia coli* (*E. coli*), and a gram-positive, *Bacillus cereus*, by the disc diffusion method. Nutrient agar medium plates were prepared, sterilized, and allowed to solidify. Once set, bacterial cultures were swabbed on these plates. Then, fractions of either pure PMMA or silver-PMMA nanocomposite film were placed in the nutrient agar plate, which was then incubated at 37° C. for 24 hours. Zones of inhibition were observed, and are depicted in FIG. 4.

Example 4

Microbiological Testing of Water

To treat the tap water with the greener nanocomposite film, a 1×1 cm square of the film was soaked in 50 ml tap water in a glass Erlenmeyer flask for 48 hours. Then, the treated water was tested for microorganism activity.

To prepare 250 ml general purpose nutrient agar (NA) medium, we dissolved 7 g of the agar medium in 250 ml of distilled water. To prepare 250 ml Eosin methylene blue (EMB) agar medium for the isolation of coliforms and *E. coli*, we dissolved 12.87 g of the agar medium in 250 ml of distilled water. For Mueller-Hinton agar (MH) medium, we dissolved 9.5 g of the agar medium in 250 ml of distilled water. Each of these was subsequently autoclaved, and for testing, we added 100 μl tap water (untreated or treated), mixed thoroughly, and poured each medium mixture into a petri dish. The plates were then incubated at 37° C. for 24-48 hours.

Figure 5:
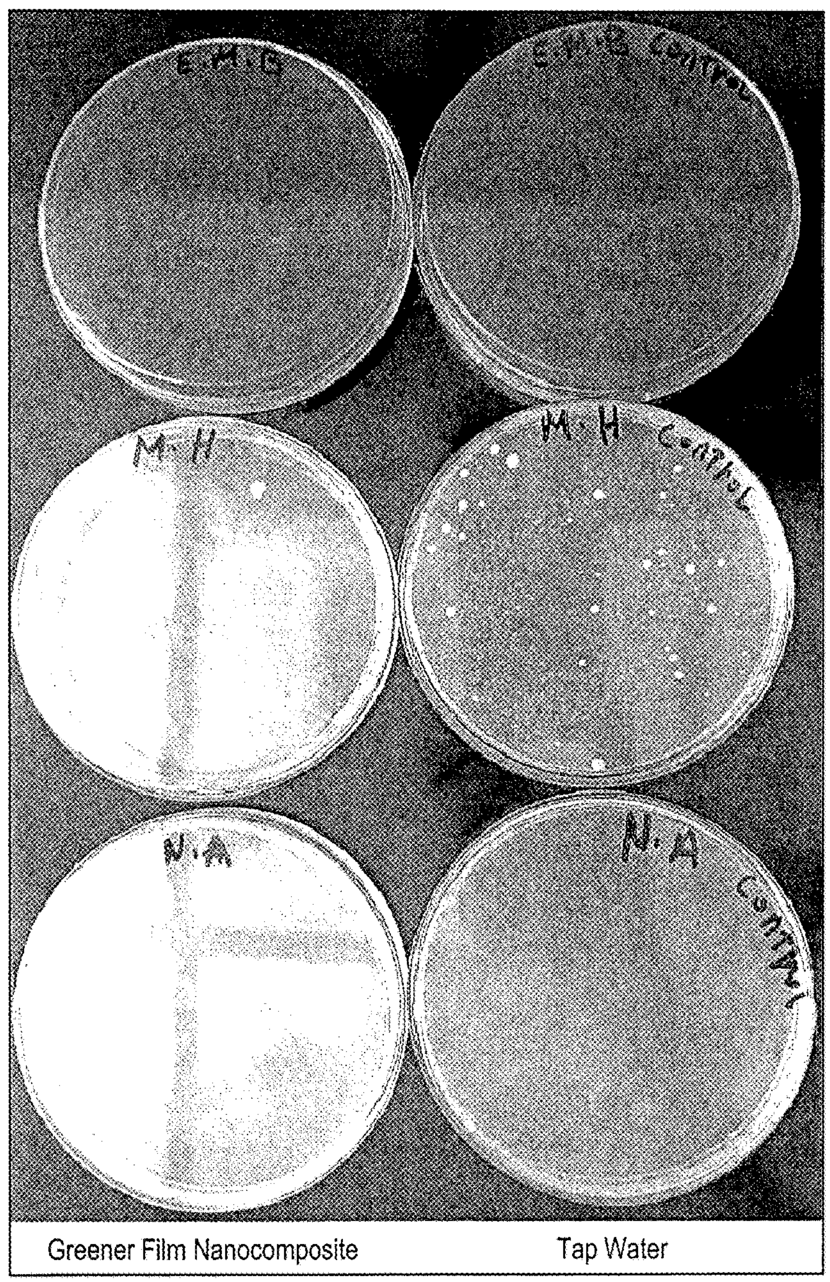
FIG. 5 is a photograph comparing untreated tap water samples (right-hand column) with samples of tap water treated with the silver-PMMA nanocomposite film (left-hand column), synthesized as described herein, wherein E.M.B. signifies Eosin Methylene Blue media, M.H. signifies Mueller-Hinton agar media, and N.A. signifies nutrient agar media.

The results demonstrate that the plates with treated water have no growth of micro-organisms, in contrast with the plates with ordinary (untreated) tap water. See FIG. 5.

As noted above, TGA was performed comparing the Ag/PMMA nanocomposites and the pure PMMA. The results demonstrate that the AgNPs/PMMA nanocomposite has higher thermal stability than the PMMA polymer. See FIG. 3. We believe the high thermal stability of the polymer itself is further enhanced by the presence of silver as nano-filler in the polymer matrix.

The synthetic technique discussed and set forth here is non-toxic, ecologically friendly, without no use of lethal chemicals, effectively providing greener silver-PMMA nanocomposite film with a higher thermal stability than that of PMMA polymer alone. The resulting nanocomposite films showed significant antibacterial activities with regard to microbes in water. This presents a promising potential utilization of greener nanocomposite for use, for example, in decontamination of water, water channels and water containers, and filters, as well as general water and wastewater treatment.

It is to be understood that the synthesis of a silver-PMMA nanocomposite film using herbal extract is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method for synthesis of a silver-PMMA nanocomposite film, comprising the steps of:

dissolving silver nitrate in water to obtain an aqueous solution of silver ions;

extracting buds of *Aristolochia bracteolate* in water to obtain an aqueous *Aristolochia* extract;

mixing the aqueous solution of silver ions with the aqueous *Aristolochia* extract to obtain silver nanoparticles in water;

mixing the silver nanoparticles in water with poly (methyl methacrylate) [PMMA] in an organic solvent at 80° C. to obtain a colloidal solution of a nanocomposite of silver nanoparticles and PMMA;

casting the colloidal solution on a support; and evaporating the organic solvent at room temperature to obtain a silver-PMMA nanocomposite film;

wherein the step of dissolving silver nitrate in water comprises the step of dissolving silver nitrate in distilled water at 60° C. under continuous stirring.

2. The method for synthesis of a silver-PMMA nanocomposite film according to claim 1, wherein the organic solvent comprises N',N-dimethylformamide (DMF).

3. The method for synthesis of a silver-PMMA nanocomposite film according to claim 1, wherein the silver nanoparticles have a particle size between 12 nm and 50 nm.

4. The method for synthesis of a silver-PMMA nanocomposite film according to claim 1, wherein the step of extracting buds of *Aristolochia bracteolate* comprises the steps of:

washing, drying, and grinding the buds;

soaking the ground buds in boiled distilled water overnight to obtain a crude extract; and filtering the crude extract and retaining the filtrate as the aqueous *Aristolochia* extract.

5. A method of inhibiting microbial growth in water, comprising the step of soaking a sample of the silver-PMMA nanocomposite film according to claim 1 in the water.

6. A method of inhibiting growth of gram-positive bacteria in a medium, comprising the step of incubating a sample of the silver-PMMA nanocomposite film according to claim 1 in the medium for 24 hours.

7. A method of inhibiting growth of gram-negative bacteria in a medium, comprising the step of incubating a sample of the silver-PMMA nanocomposite film according to claim 1 in the medium for 24 hours.

* * * * *